United States Patent
Jansen et al.

(10) Patent No.: US 11,530,877 B2
(45) Date of Patent: Dec. 20, 2022

(54) HEAT EXCHANGE USING PHASE CHANGE MATERIAL

(71) Applicant: Lockheed Martin Corporation, Bethesda, MD (US)

(72) Inventors: Eugene Charles Jansen, Stafford, VA (US); Cathleen Needham, Vienna, VA (US); Scott Morris Maurer, Haymarket, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 76 days.

(21) Appl. No.: 15/660,524

(22) Filed: Jul. 26, 2017

(65) Prior Publication Data
US 2018/0031326 A1    Feb. 1, 2018

Related U.S. Application Data

(60) Provisional application No. 62/385,607, filed on Sep. 9, 2016, provisional application No. 62/369,237, filed on Aug. 1, 2016.

(51) Int. Cl.
*F28D 20/00*      (2006.01)
*F28D 5/02*      (2006.01)
(Continued)

(52) U.S. Cl.
CPC ............... *F28D 5/02* (2013.01); *C07C 9/22* (2013.01); *F28D 20/023* (2013.01); *F28F 13/003* (2013.01); *B32B 2266/045* (2013.01); *F28D 1/05366* (2013.01); *F28D 7/0008* (2013.01); *F28D 2020/0017* (2013.01);
(Continued)

(58) Field of Classification Search
CPC ...... F28D 1/05366; F28D 5/02; F28D 7/0008; F28D 9/0062; F28D 20/023; F28D 2020/0013; F28D 2020/0017; F28D 2021/0061; B32B 2266/045; C07C 9/22; F28F 1/022; F28F 1/40; F28F 1/42; F28F 13/003; F28F 21/02; F28F 21/084;
(Continued)

(56) References Cited

U.S. PATENT DOCUMENTS 2,151,540 A * 3/1939 Varga ................. F28F 3/02
                                          138/117
3,476,179 A * 11/1969 Franz ................. F28D 9/0037
                                          165/166
(Continued)

FOREIGN PATENT DOCUMENTS

| EP | 0010819 A1 | 5/1980 |
| EP | 1657087 A1 | 5/2006 |
| FR | 2975177 A1 | 11/2012 |

OTHER PUBLICATIONS

Irwin, Matthew A. Testing of Carbon Foam with a Phase Change Material for Thermal Energy Storage. A thesis presented to the faculty of the Russ College of Engineering and Technology of Ohio University. Aug. 2014. 84 pages.
(Continued)

*Primary Examiner* — Travis Ruby
(74) *Attorney, Agent, or Firm* — Baker Botts L.L.P.

(57) ABSTRACT

A heat exchange device comprising phase change material-impregnated heat conductive foam disposed between fluid stream channels in a heat exchanger element.

13 Claims, 5 Drawing Sheets

(51) Int. Cl.
*F28F 13/00* (2006.01)
*F28D 20/02* (2006.01)
*C07C 9/22* (2006.01)
*F28F 1/02* (2006.01)
*F28D 1/053* (2006.01)
*F28D 7/00* (2006.01)
*F28D 21/00* (2006.01)

(52) U.S. Cl.
CPC ...... *F28D 2021/0061* (2013.01); *F28F 1/022* (2013.01); *F28F 2255/16* (2013.01); *Y02E 60/14* (2013.01)

(58) Field of Classification Search
CPC ............... F28F 2255/08; F28F 2255/16; F28F 2275/04; F28F 2275/10
See application file for complete search history.

(56) References Cited

U.S. PATENT DOCUMENTS

| | | | | |
|---|---|---|---|---|
| 3,587,732 A * | 6/1971 | Burne | ............ | F28D 7/1669 165/158 |
| 3,825,061 A * | 7/1974 | Bathla | ............ | F28D 9/0081 165/166 |
| 3,907,032 A * | 9/1975 | DeGroote | ............ | F28D 1/05366 165/143 |
| 4,250,958 A * | 2/1981 | Wasserman | ............ | F28D 20/02 126/618 |
| 4,259,401 A * | 3/1981 | Chahroudi | ............ | E04C 1/392 126/618 |
| 4,401,155 A * | 8/1983 | Royal | ............ | F28D 9/0081 165/166 |
| 4,709,752 A * | 12/1987 | Schroder | ............ | A45D 20/12 165/47 |
| 5,388,329 A * | 2/1995 | Randlett | ............ | B21C 3/16 29/890.049 |
| 6,035,928 A * | 3/2000 | Ruppel | ............ | F28D 1/0246 165/152 |
| 6,037,032 A * | 3/2000 | Klett | ............ | B32B 5/18 428/71 |
| 6,405,793 B1 * | 6/2002 | Ghodbane | ............ | B60H 1/00007 165/140 |
| 6,858,280 B2 * | 2/2005 | Allen | ............ | F17C 13/001 428/69 |
| 7,073,570 B2 * | 7/2006 | Yu | ............ | F28D 1/0443 165/140 |
| 9,080,818 B2 * | 7/2015 | Maurer | ............ | F28F 1/122 |
| 9,255,740 B2 * | 2/2016 | Bellenfant | ............ | B60H 1/00328 |
| 10,093,843 B2 * | 10/2018 | Eliyahu | ............ | B29C 70/58 |
| 2002/0002837 A1 * | 1/2002 | Shirota | ............ | B60H 1/005 62/430 |
| 2002/0088246 A1 * | 7/2002 | Bureau | ............ | B60H 1/00321 62/434 |
| 2003/0121637 A1 * | 7/2003 | Lee | ............ | F28D 20/021 165/10 |
| 2004/0104020 A1 * | 6/2004 | Haller | ............ | F28D 1/0476 165/177 |
| 2004/0244196 A1 * | 12/2004 | Kaimura | ............ | B21B 1/227 29/890.052 |
| 2006/0283585 A1 * | 12/2006 | Smith | ............ | F28F 3/025 165/177 |
| 2006/0293086 A1 * | 12/2006 | Haws | ............ | F28F 13/003 257/E23.089 |
| 2007/0284095 A1 * | 12/2007 | Wang | ............ | F28D 7/10 165/166 |
| 2008/0099187 A1 * | 5/2008 | Rini | ............ | F28D 20/023 165/104.17 |
| 2009/0095015 A1 * | 4/2009 | Kerler | ............ | F28D 1/05391 62/524 |
| 2009/0294110 A1 * | 12/2009 | Foust | ............ | F03G 7/05 165/152 |
| 2009/0308582 A1 * | 12/2009 | Nagurny | ............ | B21D 53/02 165/167 |
| 2010/0000707 A1 * | 1/2010 | Tsubone | ............ | F28D 20/00 165/10 |
| 2010/0157525 A1 | 6/2010 | Ullman et al. | | |
| 2011/0011570 A1 | 1/2011 | Levings et al. | | |
| 2011/0132016 A1 * | 6/2011 | Chandler | ............ | F28D 20/023 62/259.1 |
| 2012/0138275 A1 * | 6/2012 | Biggin | ............ | C08J 9/0004 165/104.34 |
| 2012/0199335 A1 * | 8/2012 | Maurer | ............ | F28D 7/0058 165/185 |
| 2012/0240919 A1 | 9/2012 | Baumann | | |
| 2012/0282454 A1 * | 11/2012 | Jansen | ............ | C09J 5/00 428/307.7 |
| 2014/0230455 A1 * | 8/2014 | Chandler | ............ | F25B 21/02 62/3.3 |
| 2015/0285564 A1 * | 10/2015 | Wood | ............ | F28D 20/021 165/10 |
| 2018/0031326 A1 * | 2/2018 | Jansen | ............ | F28D 20/023 |
| 2019/0003781 A1 * | 1/2019 | Caniere | ............ | B60H 1/005 |

OTHER PUBLICATIONS

European Search Report and Written Opinion for EP Pat. App. No. 17184065 completed on Jan. 23, 2018.

Irwin, Matthew A. Testing of Carbon Foam with a Phase Change Material for Thermal Energy Storage. Dept. of Mechanical Engineering, Russ College of Engineering and Technology. Aug. 2014. 84 pages.

\* cited by examiner

HEAT EXCHANGE USING PHASE CHANGE MATERIAL

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND

Field

This application relates generally to the use of phase change material in a heat exchange device.

Description of Related Art Including Information Disclosed Under 37 CFR 1.97 and 1.98

Heat exchange devices transfer heat between fluid flows. The fluid flows may be arranged in cross flow, counter-current flow, or parallel (co-current) flow configuration and may be separated by solid walls to prevent mixing. The walls separating the fluid flows may include materials and structures conducive to heat transfer between the fluid flows. In heat exchange devices comprising brazed aluminum fin heat exchangers (BAHX), the fluid flows may be directed through channels comprising aluminum fin arrays of various configurations brazed onto parting sheets.

Phase change materials are known to be capable of storing a significant amount of latent heat energy relative to mass and volume, but the thermal conductivity of phase change materials is typically very poor. Phase change materials are generally categorized under four nominal categories: organic materials, eutectic solutions, salt hydrates, and high temperature salts. Phase change materials are distinguishable from each other by their reactivity with other materials and their melting temperatures.

Graphite, and metallic foams are known for use in heat exchange applications due to their high thermal conductivity, low chemical reactivity, and light weight.

SUMMARY

A heat exchange device is provided for transferring heat between a heat exchanger element and a fluid flowing along the element. The device comprises a first fluid stream channel, a second fluid stream channel, and a receptacle disposed between the first and second fluid stream channels. Heat conductive foam is disposed in the receptacle, and phase change material is impregnated in the heat conductive foam.

A method is provided for making a heat exchange device. The method includes the steps of providing heat conductive foam in a receptacle disposed between first and second fluid stream channels, and impregnating the heat conductive foam with phase change material.

DRAWING DESCRIPTIONS

DETAILED DESCRIPTION

Figure 1:
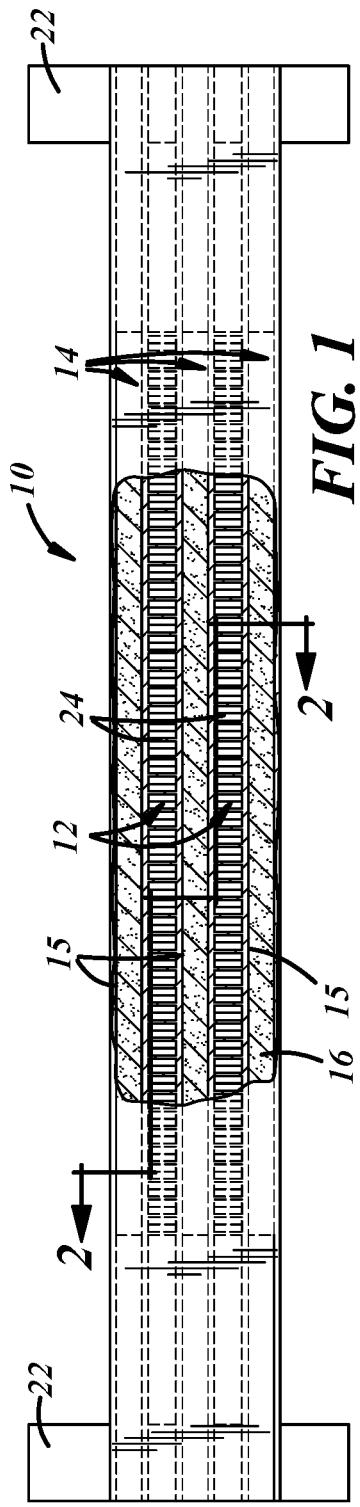
FIG. 1 is a partially cut-away side view of a first embodiment of a heat exchange device comprising phase change material impregnating a heat conductive foam disposed in receptacles in heat exchanger elements of the heat exchange device, the receptacles being elongated voids or channels in multi-hollow extrusions.

A first embodiment of a heat exchange device that transfers heat between fluid streams flowing along or through the device is generally indicated at 10 in FIGS. 1-6. A second embodiment is generally indicated at 10' in FIG. 7, and a third embodiment is generally indicated at 10" in FIGS. 8 and 9. Reference numerals with the designation prime (') in FIG. 7 and double-prime (") in FIGS. 8 and 9 indicate alternative configurations of elements that also appear in the first embodiment. Unless indicated otherwise, where a portion of the following description uses a reference numeral to refer to FIGS. 1-6, that portion of the description applies equally to elements designated by primed numerals in FIG. 7 and the double-primed numerals in FIGS. 8 and 9.

Figure 4:
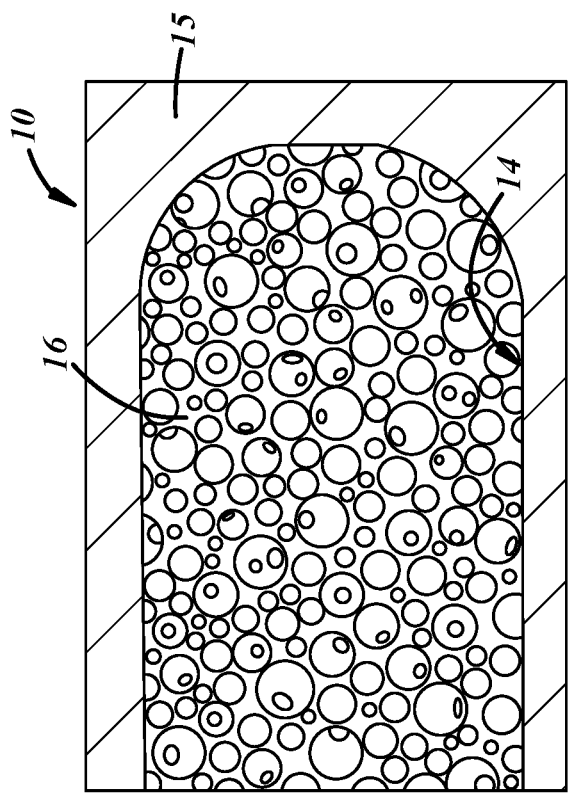
FIG. 4 is a partial cross-sectional magnified view of the portion of the heat exchange device element and heat conductive foam of the heat exchange device of FIG. 1 enclosed in box 4 of FIG. 3.
Figure 6:
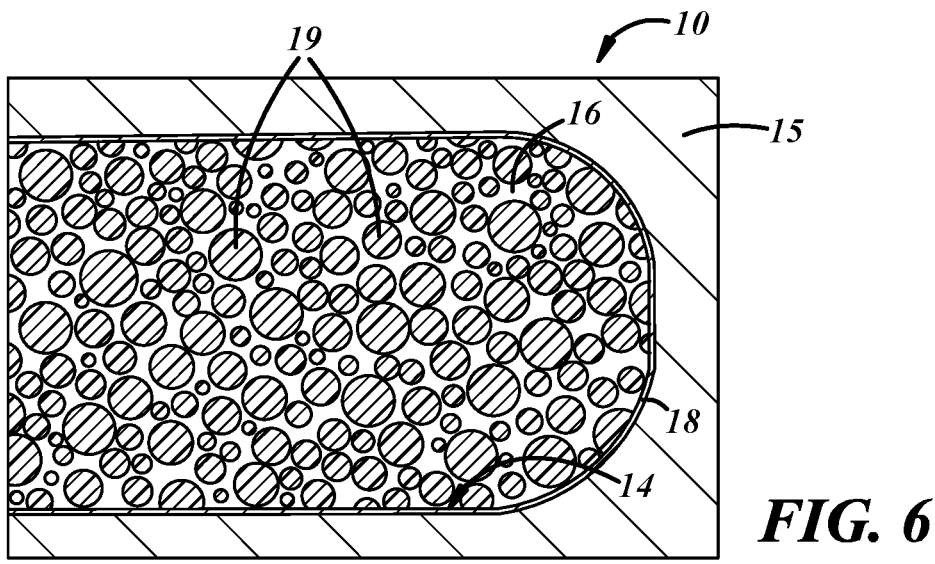
FIG. 6 is the partial cross-sectional magnified view of FIG. 4 with a brazing or soldering filler metal layer shown between the receptacle and the phase change material-impregnated heat conductive foam.

The device 10 may comprise aluminum, copper, stainless steel, and/or any other suitable material suitable for use in constructing heat exchange devices and, as shown in FIG. 1, may include a plurality of fluid stream channels 12 separated by a plurality of receptacles 14 disposed between the fluid stream channels 12. As best shown in FIG. 4, the device 10 may further include heat conductive foam 16 disposed in the receptacles 14. The heat conductive foam 16 may preferably comprise graphite foam, but may instead or additionally include any suitable aluminum and/or metallic foam or foam component. As best shown in FIG. 6, a brazing or soldering filler metal layer 18 may be disposed between the heat conductive foam 16 and the receptacles 14 to increase retention, minimize interfacial resistance, and increase thermal conductivity between the foam 16 and receptacles 14.

Figure 7:
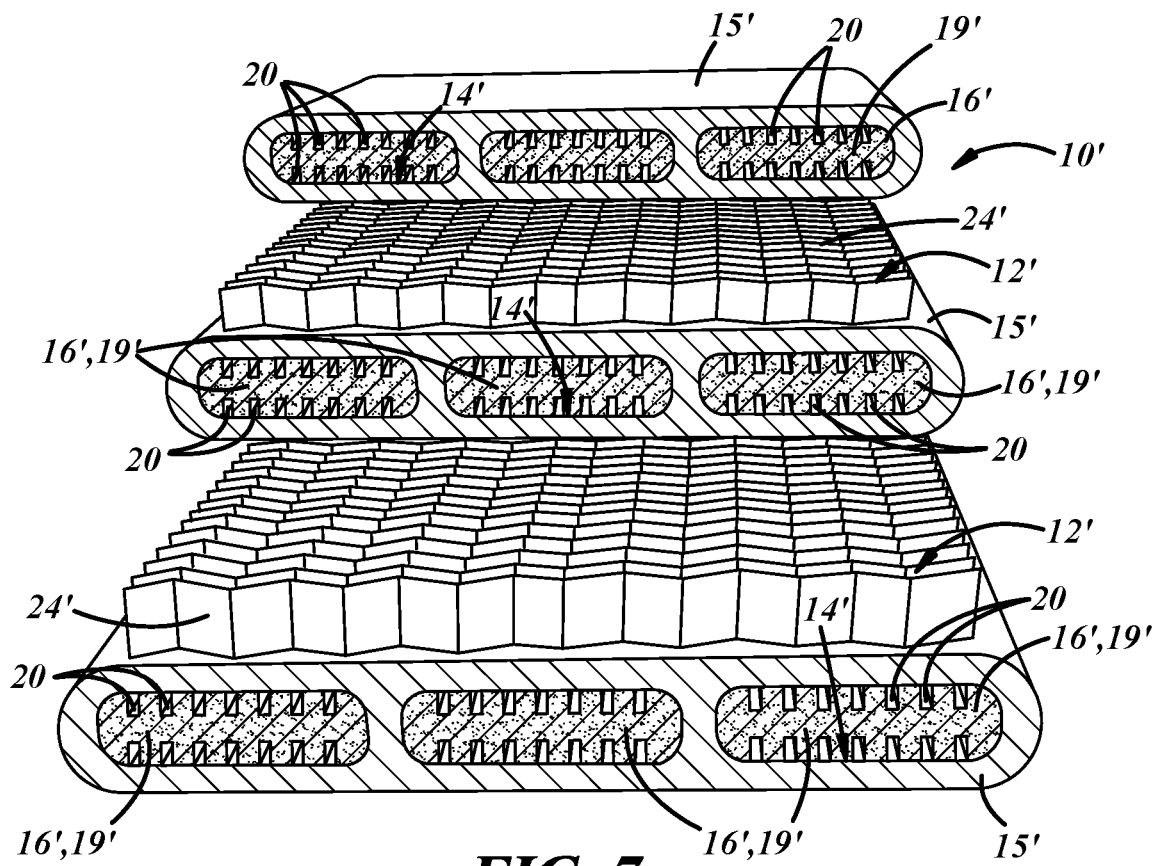
FIG. 7 is an exploded cross-sectional view of an alternative heat exchange device embodiment similar to the embodiment of FIG. 1 but with slots formed or machined into the impregnated heat conductive foam.

As best shown in FIG. 7, and according to the second heat exchange device embodiment, the heat conductive foam 16' may include a plurality of generally parallel rectangular grooves 20 shaped and positioned to allow for expansion and contraction of the foam 16'.

Figure 5:
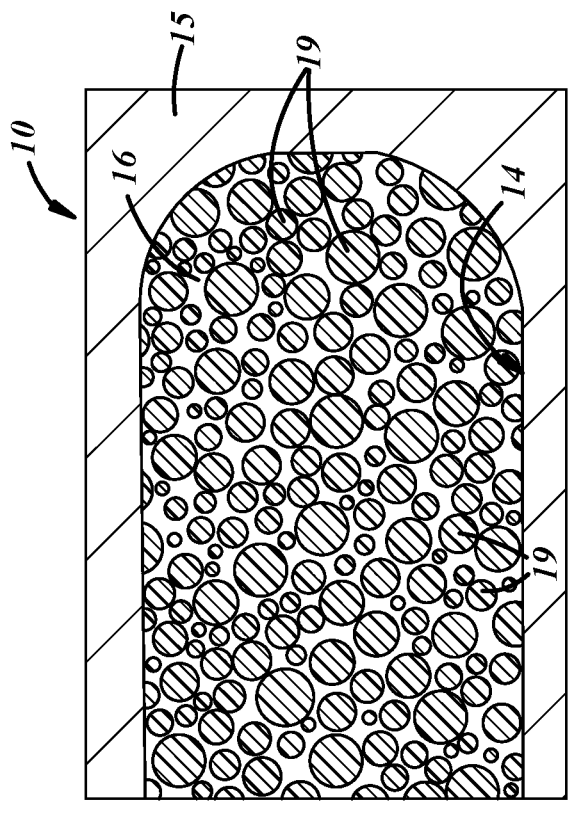
FIG. 5 is the partial cross-sectional magnified view of FIG. 4 with phase change material shown impregnating the heat conductive foam.

The heat conductive foam 16 may be force-fit, e.g., press-fit or stamped, into each receptacle 14 of the plurality of receptacles 14 to provide an interference fit between the receptacles 14 and the heat conductive foam 16. As best shown in FIG. 5, the heat conductive foam 16 may be impregnated with hexadecane 19 and/or one or more other suitable phase change materials selected from four nominal categories of phase change materials known in the art: organic materials, eutectic solutions, salt hydrates, and high temperature salts.

Figure 2:
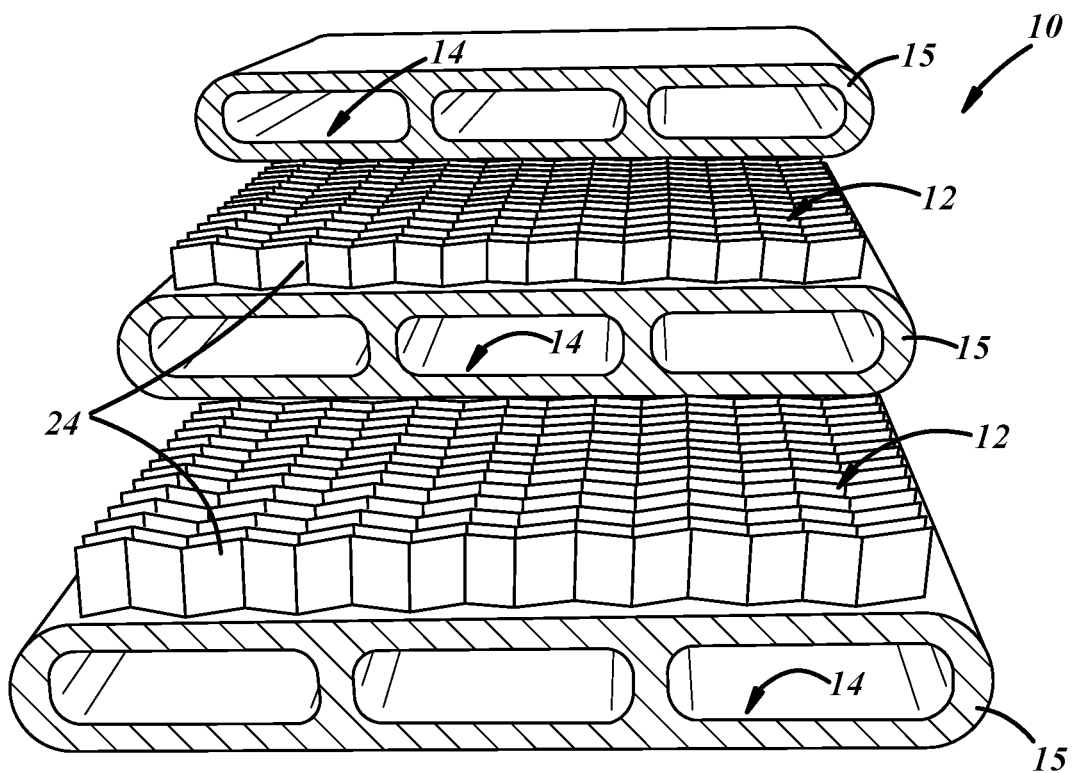
FIG. 2 is an exploded cross-sectional view of the heat exchanger elements of the heat exchange device of FIG. 1, taken along line 2-2 of FIG. 1, with the heat conductive foam and phase change material removed for clarity.
Figure 3:
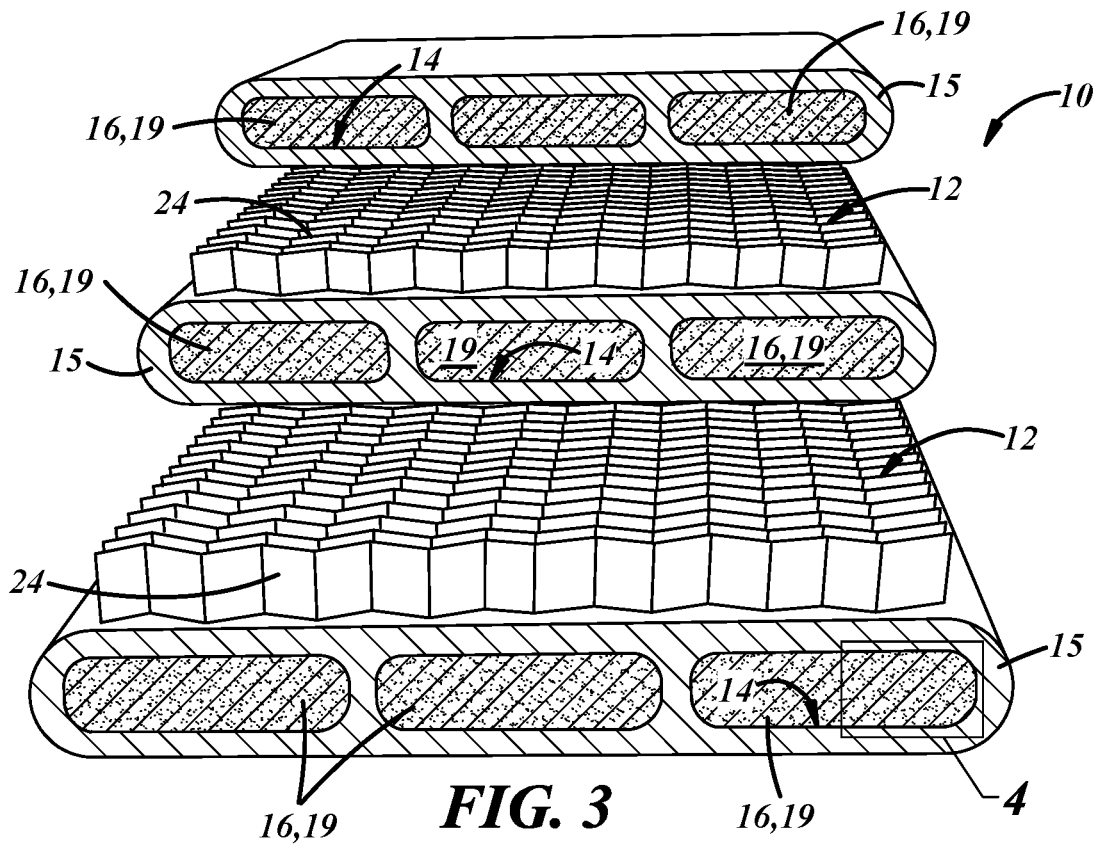
FIG. 3 is a cross-sectional view of the heat exchanger elements and phase change material-impregnated heat conductive foam of the heat exchange device of FIG. 1, taken along line 2-2 of FIG. 1.

The receptacles 14 for receiving heat conductive foam 16 and phase change material 19 may comprise parallel elongated voids or channels formed in metal extrusions, e.g., in multi-hollow extrusions (MHEs) 15. Each of the fluid stream channels 12 may be disposed between adjacent metal extrusions 15 and may be defined by inner side wall surfaces of baffles connecting the adjacent metal extrusions 15, and outer surfaces of upper and lower walls of the adjacent metal extrusions 15, as is best shown in FIG. 1. As is also best shown in FIG. 1, the metal extrusions 15 may extend between and be supported in generally parallel, spaced-apart positions by end manifolds 22. As best shown in FIGS. 2 and 3, heat conductive fin arrays 24 may be disposed within and extend across the fluid stream channels 12 between the adjacent metal extrusions 15. The fin arrays 24 may be of any suitable configuration and spacing and may preferably comprise aluminum. For example, while the fin arrays 24 shown in the drawings are oriented cross flow, in other embodiments they may be oriented counter-current or co-current flow.

Figure 8:
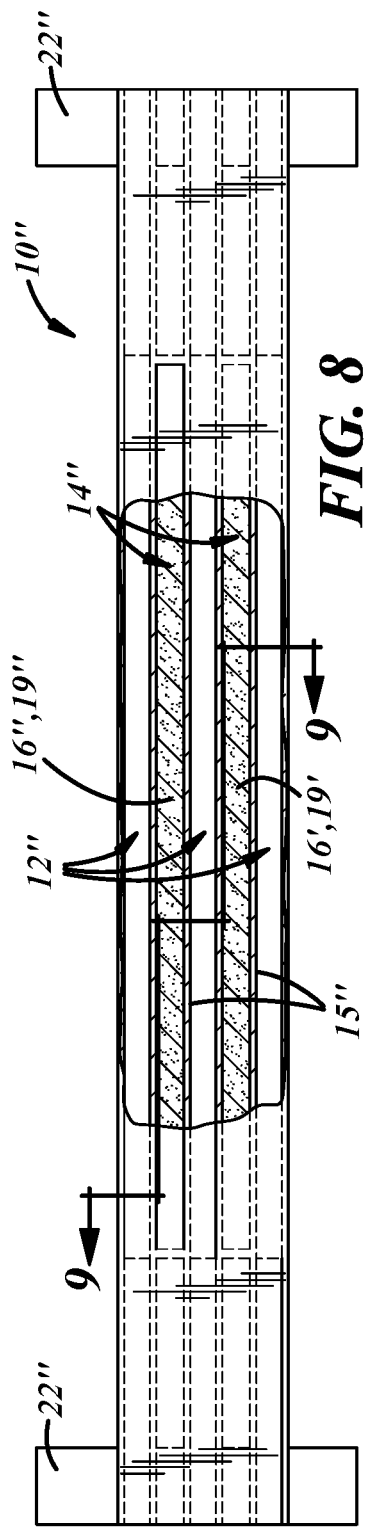
FIG. 8 is a partially cut-away side view of a further alternative heat exchange device embodiment comprising layers of phase change material-impregnated heat conductive foam disposed between heat exchanger elements of the heat exchange device.
Figure 9:
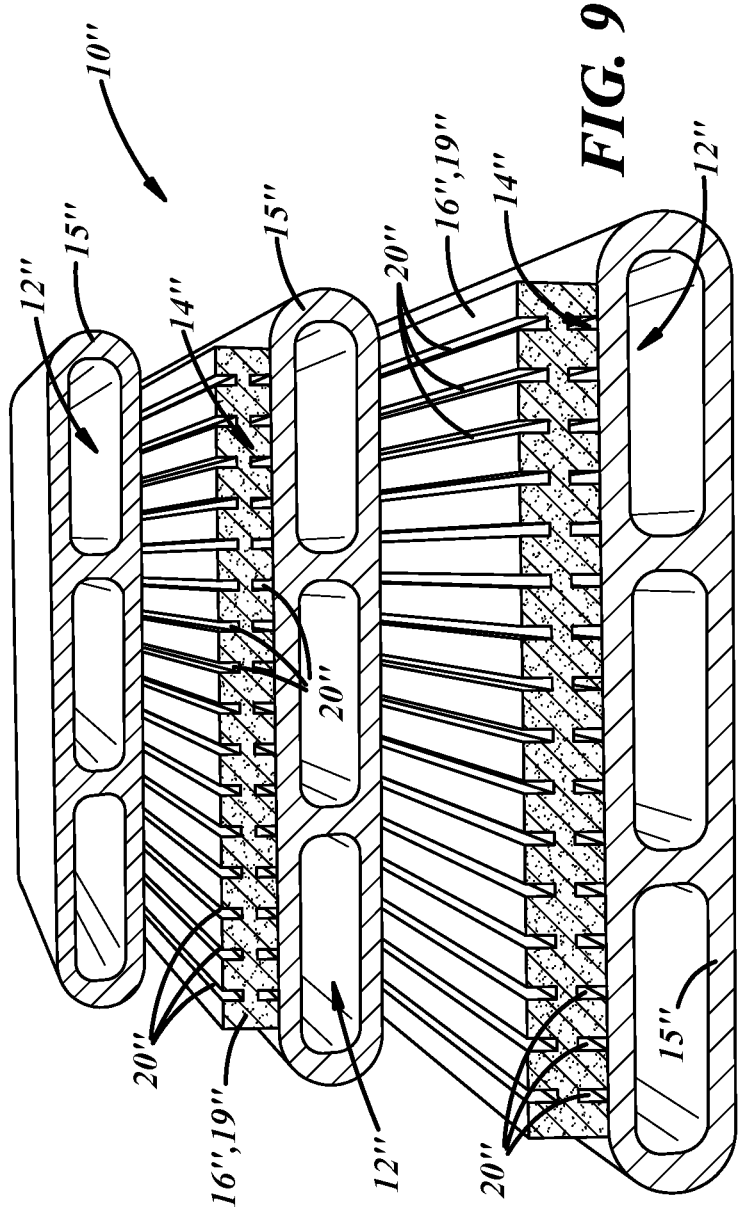
FIG. 9 is a cross-sectional view of the heat exchanger elements and phase-change material-impregnated conductive foam layers of the heat exchange device of FIG. 7, taken along line 9-9 of FIG. 8.

Alternatively, and as shown in the embodiment of FIGS. 8 and 9, the fluid stream channels 12" may comprise elongated voids or channels formed in multi-hollow extrusions (MHEs) 15", and the receptacles 14" carrying phase change material 19" impregnated heat conductive foam 16" may be interspersed between the MHEs 15". According to this embodiment, each receptacle 14" for receiving heat conductive foam 16" and phase change material 19" may comprise an elongated channel disposed between adjacent fluid stream channels 12", and may be defined by inner side wall surfaces of baffles and outer surfaces of upper and lower walls of the metal extrusions 15" defining the fluid stream channels 12", as is best shown in FIG. 9. Alternatively, and as shown in FIG. 9, the heat conductive foam 16" may include a plurality of generally parallel rectangular grooves 20" shaped and positioned to allow for expansion and contraction of the heat conductive foam 16".

Figure 10:
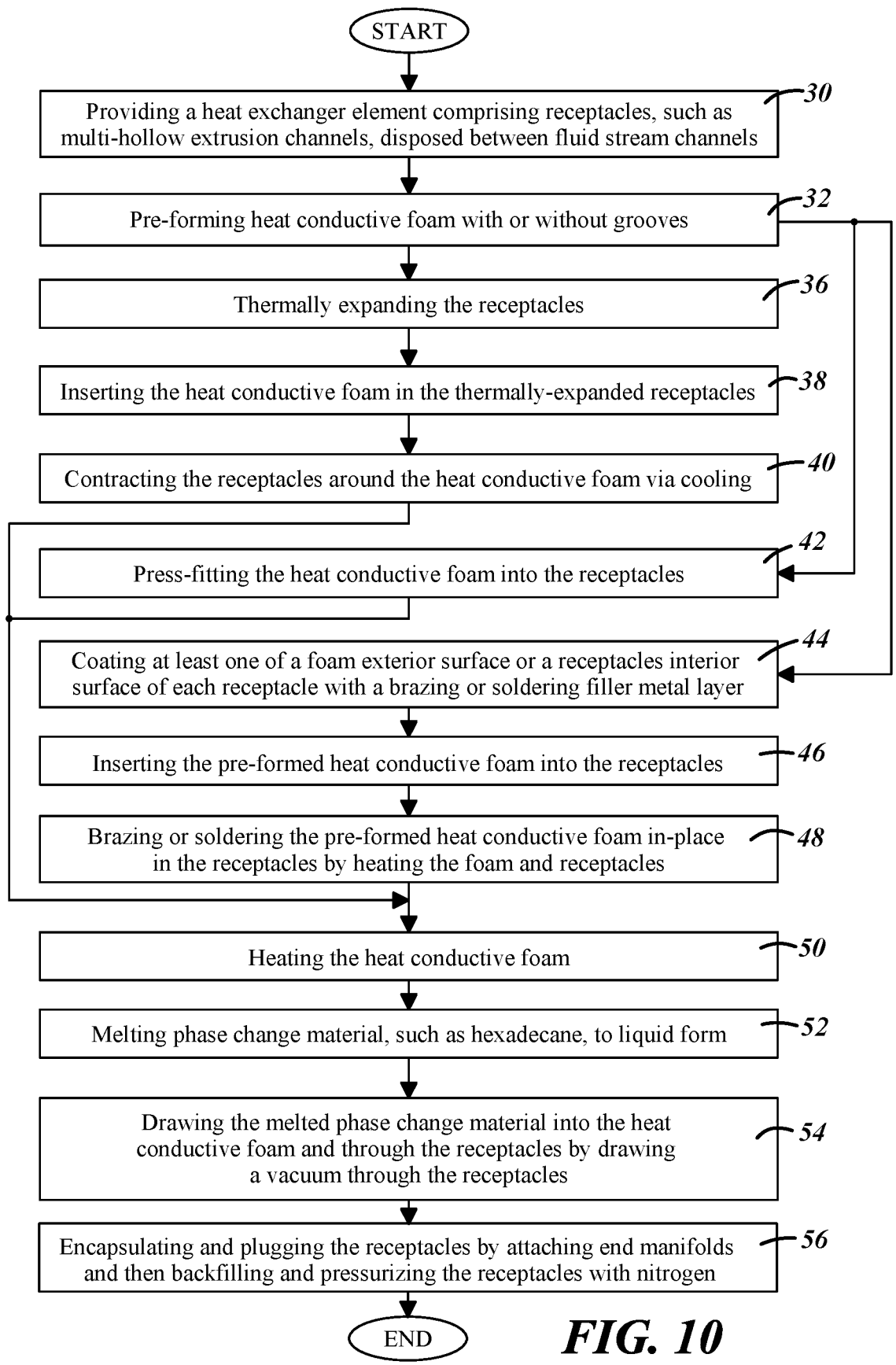
FIG. 10 is a flow chart showing alternative methods for constructing a heat exchange device.

As shown in FIG. 10, the device 10 can be constructed by first providing or forming heat exchanger elements that comprise or define, at least in part, receptacles 14 disposed between fluid stream channels 12, according to action step 30. The heat exchange device 10 may be constructed via brazing, extruding, or any other suitable means known in the art. The fluid stream channels 12 and/or intervening receptacles 14 may, for example be formed in one or more multi-hollow extrusions 15 by extruding metal in such a way as to form multiple parallel elongated channels within such extrusions 15.

Heat conductive foam 16 may then be provided in the receptacles 14 according to action steps 32-40, action step 42, or action steps 44-48 of FIG. 10. To provide a tight fit between the heat conductive foam 16 and interior surfaces of the receptacles 14, the receptacles 14 may first be thermally expanded by heating, according to action step 36. The heat conductive foam 16 may then be inserted into the thermally expanded receptacles 14, according to action step 38; and the receptacles 14 then contracted around the heat conductive foam 16 by allowing the element to cool, according to action step 40. Alternatively, a tight fit may be provided between the heat conductive foam 16 and the interior surfaces of the receptacles 14 by press-fitting pre-shaped, over-sized pieces of heat conductive foam 16 into the receptacles 14, according to action step 42.

Alternatively, or in addition, the heat conductive foam 16 may be pre-formed into heat conductive foam inserts shaped to fit in the receptacles 14, according to action step 32 of FIG. 10. Exterior surfaces of the pre-formed foam inserts and/or interior surfaces of the receptacles 14 may then be coated with a brazing or soldering filler metal layer 18, according to action step 44. The pre-formed heat conductive foam inserts may then be inserted into the receptacles 14, according to action step 46, and brazed or soldered in-place in the receptacles 14. Where the foam inserts are brazed in-place in the receptacles 14, the foam inserts and receptacles 14 may be heated in a brazing oven, according to action step 48. Grooves 20 may be formed in the pre-formed conductive foam inserts as the foam inserts are pre-formed according to action step 32, or may be formed into the foam inserts after the foam inserts have been pre-formed. In either case, the grooves 20 are preferably formed before the foam inserts are inserted into the receptacles 14, according to action step 38.

The phase change material 19, e.g., hexadecane, may then be provided in, e.g., impregnated into the heat conductive foam 16 in accordance with action steps 50-54 of FIG. 10. The phase change material 19 may be incorporated into the heat conductive foam 16 by drawing a vacuum through the heat conductive foam 16 to extract any air or moisture trapped in the device 10; then melting the phase change material 19 to liquid form and drawing it into the heat conductive foam 16, according to action steps 52 and 54. The heat conductive foam 16 may be heated before impregnation, according to action step 50, to desorb any material that might have adsorbed into the heat conductive foam 16. To encapsulate and plug opposite open ends of the metal extrusions 15, end manifolds 22 may then be installed in accordance with action step 56. The end manifolds 22 may be installed by, for example, welding the end manifolds 22 onto opposite ends of the metal extrusions 15. The receptacles 14 may then be backfilled and pressurized with nitrogen, in accordance with action step 56. Backfilling and pressurizing is accomplished to prevent any moisture or air from entering the system through lifetime cycling of the heat exchange device 10.

In combination, the high thermal conductivity of the foam 16 and the high thermal energy storage properties of the phase change material 19 impregnating the foam 16, provide a heat exchange device 10 with higher duty cycle and higher peak heat duty than it would otherwise have.

This description, rather than describing limitations of an invention, only illustrates one or more embodiments of the invention recited in the claims. The language of this description is therefore exclusively descriptive and is non-limiting.

It is possible to modify this invention from what the description teaches. Within the scope of the claims, one may practice the invention other than as described above.

What is claimed is:

1. A heat exchange device for transferring heat between at least two fluid streams and a phase change material, the device comprising:
   a first extrusion comprising a plurality of first receptacles;
   a second extrusion separate from the first extrusion and comprising a plurality of second receptacles;
   a first fluid stream channel configured to receive and direct at least a portion of a first fluid stream of the at least two fluid streams through the heat exchange device, the first fluid stream channel being disposed between the first extrusion and the second extrusion;
   a second fluid stream channel configured to receive and direct at least a portion of a second fluid stream of the at least two fluid streams through the heat exchange device, the second fluid stream channel being disposed on an opposite side of the second extrusion from the first fluid stream channel;
   heat conductive foam inserts disposed in each first and second receptacles of the plurality of first receptacles and the plurality of second receptacles, wherein:
      each heat conductive foam insert comprises a shape that matches shapes of the first and second receptacles; and
      each heat conductive foam insert comprises a plurality of parallel grooves to allow for expansion and contraction of the heat conductive foam insert;
   the phase change material impregnating the heat conductive foam inserts; and
   a brazing or solder filler metal layer disposed on an inside surface of the first and second receptacles between the heat conductive foam inserts and the inside surface of the first and second receptacles;
   wherein each heat conductive foam insert disposed in the plurality of second receptacles of the second extrusion is configured to transfer heat between the first fluid stream and the second fluid stream.

2. The heat exchange device as defined in claim 1 in which the phase change material is selected from the group of such materials consisting of organic materials, eutectic solutions, salt hydrates, or high-temperature salts.

3. The heat exchange device as defined in claim 1 in which the phase change material comprises hexadecane.

4. The heat exchange device as defined in claim 1 in which each heat conductive foam inserts comprises one or more materials selected from the group of materials consisting of graphite foam, aluminum foam, or metallic foam.

5. The heat exchange device as defined in claim 4 in which each heat conductive foam insert is stamped into the plurality of first receptacles and the plurality of second receptacles.

6. The heat exchange device as defined in claim 1 in which the grooves running adjacent the receptacle walls leave spaces between the heat conductive foam insert and the walls of the receptacle.

7. The heat exchange device as defined in claim 1 in which each heat conductive foam insert is force-fit into the plurality of first receptacles and the plurality of second receptacles.

8. The heat exchange device as defined in claim 1, wherein the second extrusion is disposed between the first and second fluid stream channels.

9. The heat exchange device as defined claim 1, wherein the first and second extrusions comprise aluminum.

10. The heat exchange device as defined in claim 1, further comprising:
    a first fin array disposed in the first fluid stream channel; and
    a second fin array disposed in the second fluid stream channel.

11. The heat exchange device as defined in claim 1, further comprising a plurality of end manifolds, wherein:
    each end manifold is coupled to a respective end of the first and second extrusions; and
    the first and second extrusions are held in spaced-apart positions by the plurality of end manifolds.

12. The heat exchange device as defined in claim 1, wherein the plurality of first and second receptacles are backfilled and pressurized with nitrogen.

13. The heat exchange device as defined in claim 1, wherein:
    the plurality of first and second receptacles are elongated voids; and
    the heat conductive foam insert fill the elongated voids of the plurality of first and second receptacles.

* * * * *